(12) United States Patent
Eaton

(10) Patent No.: US 9,180,256 B2
(45) Date of Patent: Nov. 10, 2015

(54) SHEATH REMOVAL APPARATUS

(75) Inventor: Mark Eaton, Oxfordshire (GB)

(73) Assignee: OWEN MUMFORD LIMITED, Oxford (GB)

( * ) Notice: Subject to any disclaimer, the term of this patent is extended or adjusted under 35 U.S.C. 154(b) by 616 days.

(21) Appl. No.: 13/389,859

(22) PCT Filed: Aug. 10, 2010

(86) PCT No.: PCT/EP2010/061636
§ 371 (c)(1),
(2), (4) Date: Apr. 12, 2012

(87) PCT Pub. No.: WO2011/018462
PCT Pub. Date: Feb. 17, 2011

(65) Prior Publication Data
US 2012/0191048 A1 Jul. 26, 2012

(30) Foreign Application Priority Data

Aug. 10, 2009 (GB) .................................. 0913907.2

(51) Int. Cl.
A61M 5/00 (2006.01)
A61M 5/32 (2006.01)
A61M 5/46 (2006.01)

(52) U.S. Cl.
CPC ............ *A61M 5/3213* (2013.01); *A61M 5/3202* (2013.01); *A61M 5/46* (2013.01); *A61M 5/321* (2013.01); *A61M 5/3204* (2013.01)

(58) Field of Classification Search
CPC .................. A61M 2005/3247; A61M 5/3204; A61M 2005/3267; A61M 5/3257; A61M 2005/3254; A61M 5/3213; A61M 5/321; A61M 5/46; A61M 5/3202
USPC ............. 604/164.08, 187, 192, 197–199, 263
See application file for complete search history.

(56) References Cited

U.S. PATENT DOCUMENTS 5,527,294 A * 6/1996 Weatherford et al. ........ 604/198
5,681,291 A * 10/1997 Galli ............................. 604/192

(Continued)

FOREIGN PATENT DOCUMENTS

GB 2438593 A 5/2007
GB 2451662 A 2/2009

(Continued)

OTHER PUBLICATIONS

United Kingdom search report, dated Dec. 8, 2009, Application GB0913907-2.

(Continued)

Primary Examiner — Emily Schmidt
Assistant Examiner — Hamza Darb
(74) Attorney, Agent, or Firm — Young & Thompson

(57) ABSTRACT

Provided is apparatus for removing a sheath from a pre-filled syringe. The syringe has a barrel and a needle, the sheath providing a sterile cover for the needle. The apparatus comprises a housing, for enclosing the syringe barrel defining an injection end with an aperture sized to allow the sheath of an enclosed syringe to protrude therethrough, and a syringe barrel mount for retaining the syringe in the housing. The mount is slidable axially within the housing between positions towards and away from the injection end of the housing. The apparatus also comprises a biasing means, for biasing the mount away from the injection end of the housing, and latching means for latching said mount in a latched position to prevent sliding of the mount away from the injection end of the housing. The latching means is releasable from the latched position, by sliding of the mount towards the injection end. Also provided is an injection device comprising said apparatus.

9 Claims, 14 Drawing Sheets

(56) References Cited

U.S. PATENT DOCUMENTS

| | | |
|---|---|---|
| 7,976,514 B2 * | 7/2011 | Abry et al. .................... 604/246 |
| 2001/0031949 A1 | 10/2001 | Asbaghi |
| 2005/0165360 A1 * | 7/2005 | Stamp .......................... 604/187 |
| 2006/0100588 A1 | 5/2006 | Brunnberg et al. |
| 2006/0270986 A1 | 11/2006 | Hommann et al. |

FOREIGN PATENT DOCUMENTS

| | | |
|---|---|---|
| GB | 2451665 A | 2/2009 |
| WO | 01/68164 A1 | 9/2001 |
| WO | 2007/047200 A1 | 4/2007 |
| WO | 2008/029280 A2 | 3/2008 |

OTHER PUBLICATIONS

International Search Report, dated May 3, 2011, from corresponding PCT application.

* cited by examiner

SHEATH REMOVAL APPARATUS

TECHNICAL FIELD

The present invention relates to apparatus for removing a sheath from a syringe.

BACKGROUND

Various types of injection devices are available for assisting with the injection of a medicament into a patient (human or animal), and which are configured to receive a standard, pre-filled glass or plastic syringe tipped with an injection needle. These devices may have a dose setting mechanism and a main drive spring for driving a plunger into the syringe so as to expel the medicament out through the needle. Injection devices may comprise a further spring for driving the needle out of the device housing and into the patient's skin, prior to activation of the main drive spring to expel the medicament.

In order to maintain sterility prior to use, and to avoid "sticking" injuries, the pre-filled syringe is supplied to the injection device assembler with a rubber or plastic cap, known as a "sheath", covering the needle. The sheath has an interior space for containing the needle, and a sealing end that abuts the adjacent end of the syringe barrel to seal that inner space.

Immediately prior to use, a user (e.g. healthcare professional or patient) must remove the sheath to uncover the needle. This is typically achieved using a sheath removal tool that is inserted by a user into the injecting end of the device. The tool comprises a set of sprung fingers that ride over and along the sheath as the tool is pushed into the device. The fingers then snap into the junction between the syringe end and the sheath. The user can then pull out the tool, bringing the sheath with it.

Particularly in the case of expensive medicaments, it is extremely important to minimise the failure rate of assembled injection devices. Considering the sheath removal solution outlined in the previous paragraphs, it may be difficult to achieve exactly the right degree of flexibility in the fingers to ensure that they can ride over the sheath whilst still providing sufficient force to close over the junction at the rear of the sheath.

GB 2438593 (Cilag), US 2006/0100588 A1 (Brunnberg et al), WO 2007/047200 A1 (Eli Lilly) and US 2006/0270986 A1 (Hommann et al) all describe devices for housing syringes and removing sheaths therefrom. US 2001/0031949 A1 (Asbaghi) is not concerned with sheath removal but with only with preventing accidental re-use of a syringe after injection and with prevention of "stick" injuries at that time. Disclosed is a guard, a guard body and a spring. The device passively covers and protects an exposed needle post-injection by locking the guard housing over the tip of needle. This is achieved via a linear slot and cooperating plug arrangement. The slot has a latching cut out between the slot ends and a locking cut out. The locking cut out is positioned at an injection end of the device and, after use, locks the guard to the guard body to ensure that the guard completely covers the needle tip. A spring is provided to drive the guard towards the injection end of the device relative to the guard body, but this motion towards the injection end is limited by the latching cut out. To remove the sheath, the syringe is held in place by the latching cut out and, once removed, the device is arranged such that the needle tip is partially exposed beyond the guard. After injection, the locking cut out serves to keep the needle tip covered by the guard.

WO 01/68164 A1 (International Technology Group) provides a safety syringe, comprising an outer tubular protective cover sleeve for an inner syringe body, to prevent a needle "stick" injury. GB 2 451 665 A (Cilag) describes an injection device with a housing with an exit aperture covered by a cap, a syringe carrier, a needle sheath and a locking component. In use, the lock operates in conjunction with the cap. Upon removal of the cap, the lock is automatically released. Until released, the lock the serves to prevent forward motion of the syringe, thereby preventing damage to the syringe prior to use. GB 2 451 662 A (also by Cilag) describes an auto-injector device with a trigger and locking mechanism for restraining and triggering a drive spring to, inter alia, prevent forward motion of a syringe carrier before triggering. A pivoting trigger switch is mounted on a housing, between the drive spring and the syringe carrier. Upon triggering, drive is transmitted to the syringe via two rods connected by a piston so as to cause a time delay.

SUMMARY

It is an object of the present invention to provide an apparatus, capable of removing a sheath, that is both easy to use and reliable, reducing the failure rate of injection devices.

According to a first aspect of the present invention there is provided an apparatus for removing a sheath from a pre-filled syringe having a barrel and a needle, the sheath providing a sterile cover for the needle, the apparatus comprising:
- a housing for enclosing the syringe barrel defining an injection end with an aperture sized to allow the sheath of an enclosed syringe to protrude therethrough;
- a syringe barrel mount for retaining the syringe in the housing and being slidable axially within the housing between positions towards and away from the injection end of the housing;
- biasing means for biasing the mount away from the injection end of the housing; and
- latching means for latching said mount in a latched position to prevent sliding of the mount away from the injection end of the housing, the latching means being releasable from the latched position, by sliding of the mount towards the injection end.

The latching means may comprise a bushing body fixed inside the housing, within which the mount may be retained. The bushing body may have a front end, towards the injection end of the housing, and a rear end, away from the injection end of the housing, said ends overlapping said mount such that the mount is slidable axially within the bushing body between said ends.

The latching means may also comprise a resilient beam. The resilient beam may be connected to said bushing. The beam may extend axially towards the injection end of the housing. The beam may also be deflected by the mount into a first position when the latching means is in the latched position. The beam may resile to a second position when the latching means is released.

The latching means may further comprise a protrusion positioned on the mount. The protrusion may be spaced in relation to the beam on the mount, such that latching of the latching means deflects the beam into the first position. The end of beam may thereby rest against the protrusion, such that the protrusion prevents the beam from resiling to a second position, without release of the latching means. The beam may, therefore, be deflectable, by engagement with the protrusion on the mount, into a first position to thereby latch the latching means in the latched position.

The abutment of the beam against the protrusion prevents the mount from sliding, within the latching means, away from the injection end of the housing. The protrusion may be "U" shaped to suitably accommodate the end of the beam therein. The protrusion may be formed integrally with the mount.

The protrusion may also be spaced such that the beam, in its second position, is slidable past the protrusion. Upon release of the latching means, the mount may slide away from the injection end of the housing and the beam may thereby extend beyond the front end of the mount to a forward position.

The beam may comprise a hook at one end, towards the injection end of the housing. The hook may extend radially inwards with respect to the housing. The hook and the beam may be arranged to engage the front end of the mount from said forward position. The length of the beam, together with the arrangement of the hook and the front end of the mount, may be such that, upon engagement of the hook with the mount, the needle extends beyond the aperture of the housing by a predetermined amount. This amount may correspond to a suitable depth by which the needle is to pierce the skin of the patient.

The device comprises a biasing means to bias the mount away from the injection end of the housing. The biasing means may be a spring. The biasing means may be positioned between the rear end of the mount, away from the injection end of the housing, and a suitable point near or at the rear end of the bushing.

The beam may be resilient in all planes. In some embodiments, the beam is resilient radially outwards from the mount. The beam may be provided with a ramp at its end, away from the bushing body. The ramp may be angled such that the beam is deflected radially away from the mount by action of the ramp against a lip on the front end of the mount.

The protrusion may be provided with a locating ridge. The locating ridge may be orientated parallel to the longitudinal axis of the beam. This ridge may cooperate with a corresponding groove on the underside of the beam facing the mount. This assists the location of the hook with the front end of the mount.

The injection end of the housing is adapted so that, when the sheath and syringe are enclosed within the device and the latching means is in the latched position, the needle sheath is at least partially exposed beyond the aperture in the injection end of the housing.

Removal of the sheath by the user activates the device ready for injection of a patient. However, the arrangement of the housing, the mount and the latching means may be such that the needle, once the latching means has been released, is not exposed beyond the aperture in the injection end of the housing.

Also provided is an injection device comprising the apparatus and means for assisting with the injection of medicament from the syringe.

According to further aspect of the present invention there is also provided an injection device for a pre-filled syringe having a barrel, a needle and a sheath providing a sterile cover for the needle, the device comprising a housing for the syringe enclosing a mount adapted to grip the syringe barrel, the mount being retained within a bushing body fixed inside the housing and having a front end, proximal to an injection end of the housing, and a rear end, distal to the injection end of the housing, said ends overlapping said bushing body such that the mount is slidable axially within the bushing body between said ends; wherein the bushing further comprises a resilient beam extending axially towards the injection end of the housing, the beam comprising a hook at one end, distal from the bushing body, extending radially inwards; and wherein the mount further comprises a protrusion spaced in relation to the beam such that:

the end of the beam rests against the protrusion when deflected into a first position, thereby preventing the mount from sliding away from the injection end of the housing; and spaced such that the beam is slidable past the protrusion when the beam resiles to a second position, thereby allowing the mount to slide away from the injection end of the housing so that the beam extends beyond the front end of the mount;

the hook and the beam being adapted such that when the beam extends beyond the front end of the mount subsequent sliding of the mount towards the injection end of the housing engages the hook with said front end of the mount.

According to a still further aspect of the present invention, there is also provided an apparatus for removing a sheath from a pre-filled syringe having a barrel and a needle, the sheath providing a sterile cover for the needle, the apparatus comprises a housing for enclosing the syringe barrel and defining an injection end with an aperture sized to allow the sheath of an enclosed syringe to protrude therethrough;

means for retaining the syringe in the housing; and sheath removal means comprising one or more buttons positioned so that one or more cooperating wedges can be activated within the housing to press into a gap between the shoulder of the syringe barrel and the end of the sheath which adjoins said shoulder, the wedges being shaped so as to fit against the syringe shoulder and being provided with suitable edges or ramps adapted to urge the sheath from the needle as the wedges are driven radially inwards.

DETAILED DESCRIPTION

Apparatus will now be described that enables the easy and reliable removal of a sheath or cap covering a needle of a pre-filled syringe. As has already been outlined above, an assembler of injection devices (e.g. auto-injectors and the like) will typically obtain pre-filled syringes from a supplier. The assembler may have little or no influence over the design of the syringes including the sheaths, and may therefore have to ensure that its device design and assembly process is compatible with the syringe design.

Figure 1:
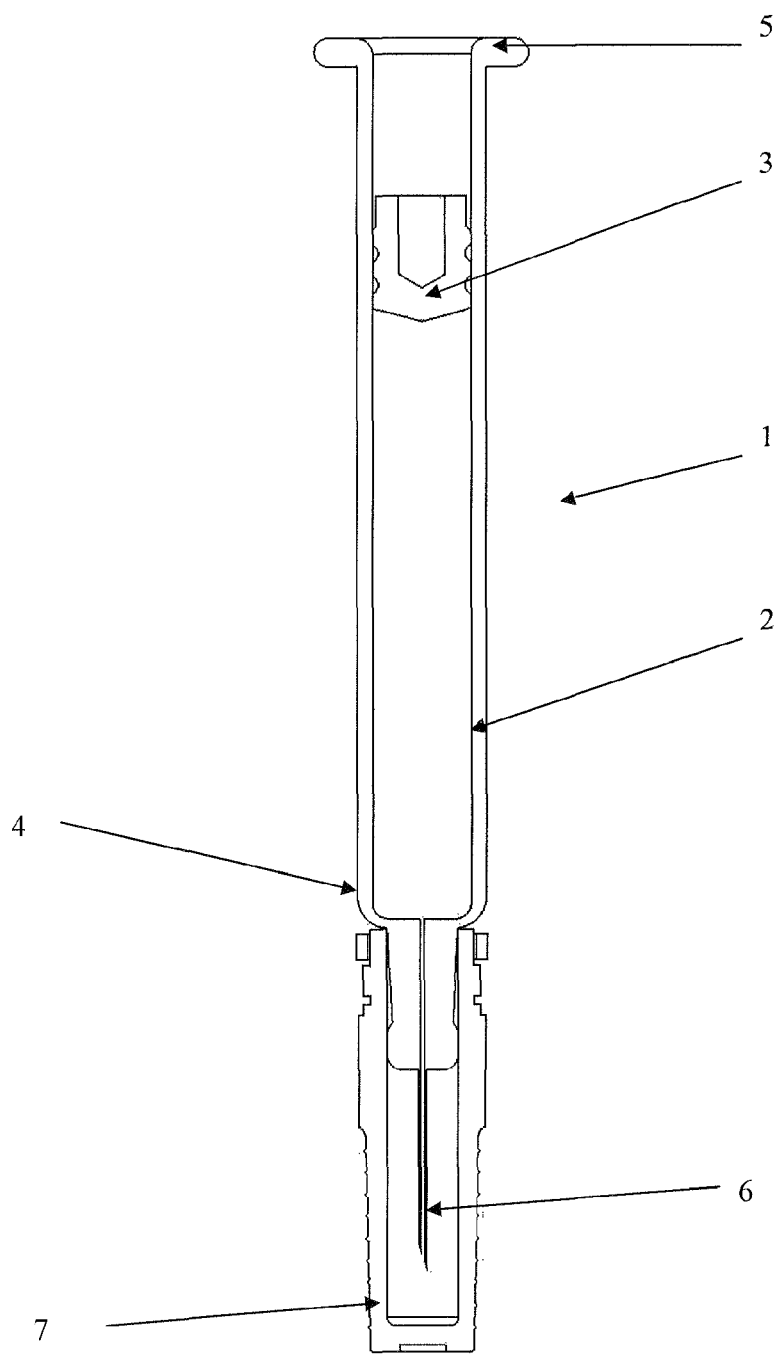
FIG. 1 illustrates a syringe with a sheath covering a syringe needle.

FIG. 1 shows a conventional syringe 1, comprising a barrel 2 containing a medicament and a piston 3 located within the barrel. The piston 3 may cooperate with a plunger (not shown) which may extend outwardly from the barrel. The syringe 1 further comprises a shoulder portion 4, wings 5 and a hypodermic needle 6 coupled to the opposite end of the barrel. A substantially solid rubber or plastics sheath 7 covers the needle 6 and seals around the shoulder 4 of the syringe barrel 2.

Figure 2:
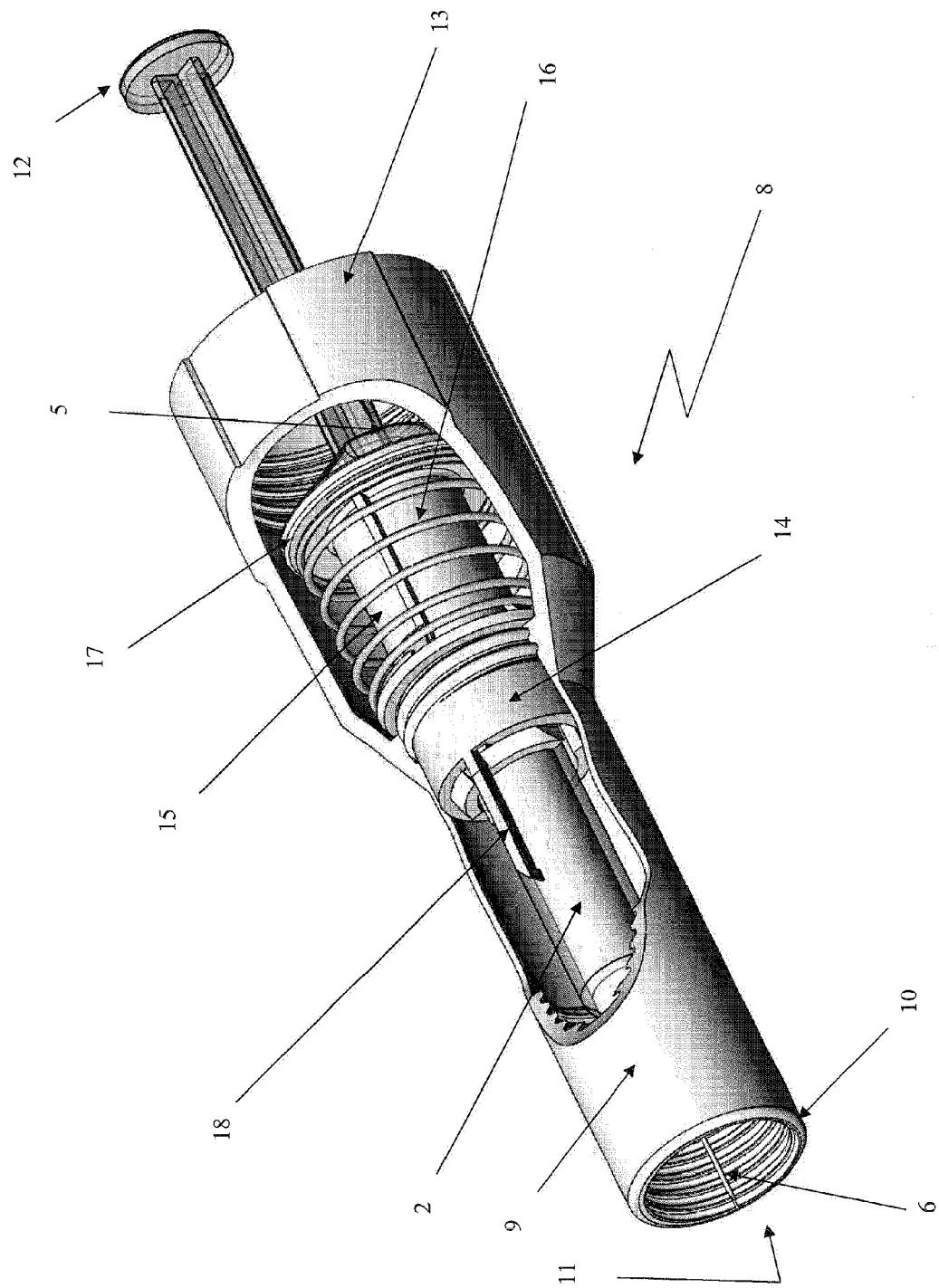
FIG. 2 illustrates, in a partially cut-away view, a syringe with attached sheath removal apparatus.

A brief overview of the sheath removal apparatus and its operation will now be provided with respect to FIGS. 2 to 5. As can be seen from FIG. 2, the apparatus 8 comprises a housing 9 with an injection end 10, having an aperture 11. When a syringe is loaded into the housing 9, the sheath protrudes through the aperture 11 and a plunger 12 extends from the opposite, plunger end 13 of the housing. A bushing 14 is immovably fixed to the inside of the housing 9 with a mount 15 slidably located within the bushing. A spring 16 pushes against an end of the bushing 14 on one side and an end of the mount 15 on the other, so as to bias the mount rearwards, away from the injection end of the housing 10, as can be seen in FIG. 2.

Figure 3:
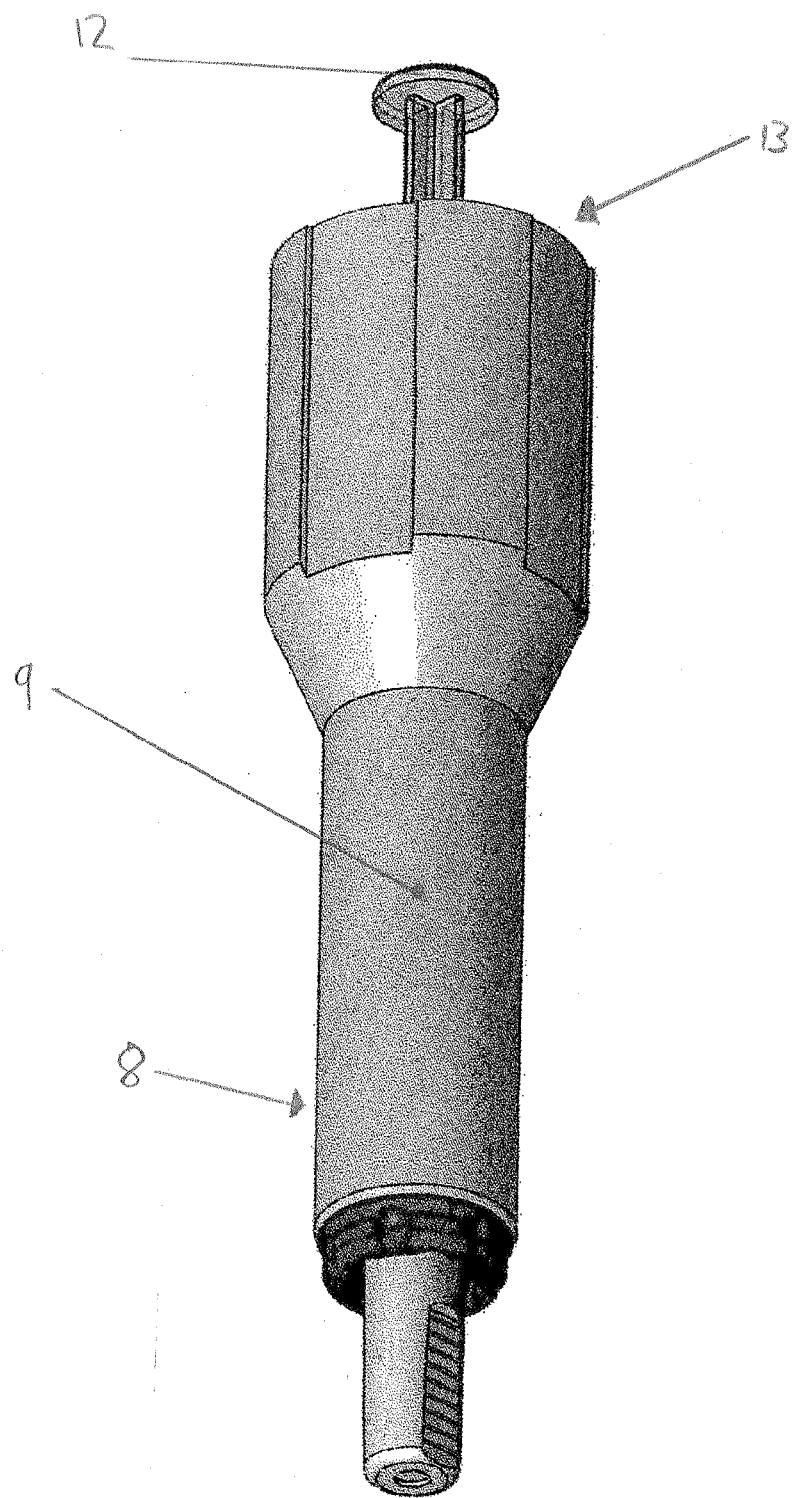
FIG. 3 illustrates a sheath removal apparatus for use with the syringe of FIG. 1.

The barrel 2 of a loaded syringe is held within the mount 15. Although the mount provides a close fit for the barrel, the wings 5 of the syringe also lock in behind a rear end 17 of the mount 15 (opposite from the injection end 10 of the housing 9), so that the syringe and the mount tend to move together. When the apparatus is loaded with the syringe, the sheath is exposed through the aperture 11 of the injection end 10 of the housing 9, as can be seen in FIG. 3.

Figure 4:
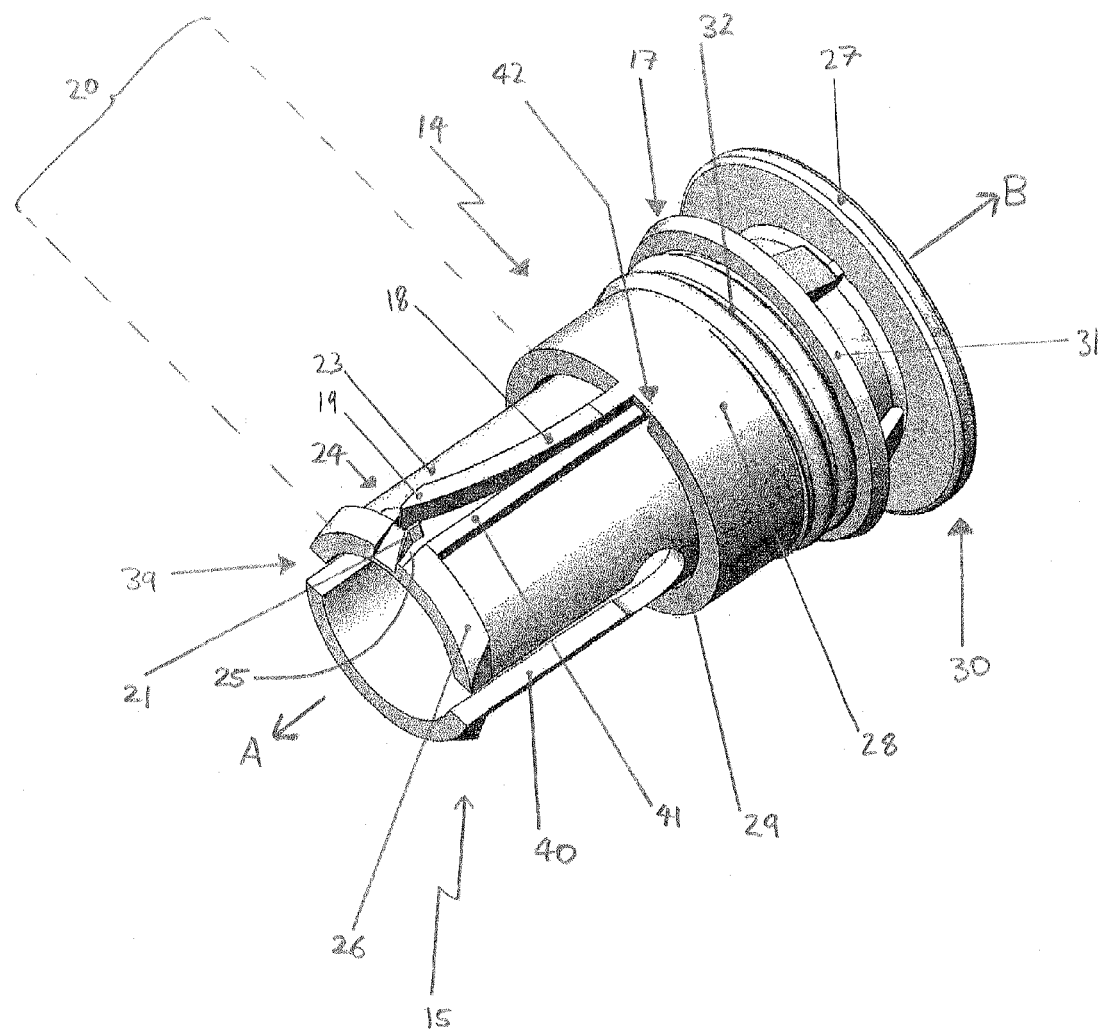
FIG. 4 illustrates, in perspective view, a mount and bushing of the apparatus of FIGS. 2 and 3 in an initial, locked configuration.

A beam 18 extends from the bushing towards the injection end of the housing. The length of the beam and its relevance during an injection is discussed further below. The beam interacts with the mount in a number of ways. The first of these is when the beam is deflected into a first position 19, which is shown in the detail of FIG. 4. This latches the bushing 14 and the mount 15 to hold the mount in a forward position 20, towards the injection end of the housing and thus prevents it sliding, under the bias of the spring 16, away from the injection end of the housing. The beam is held in this first position 19 by a protrusion 21 on the mount.

Figure 5:
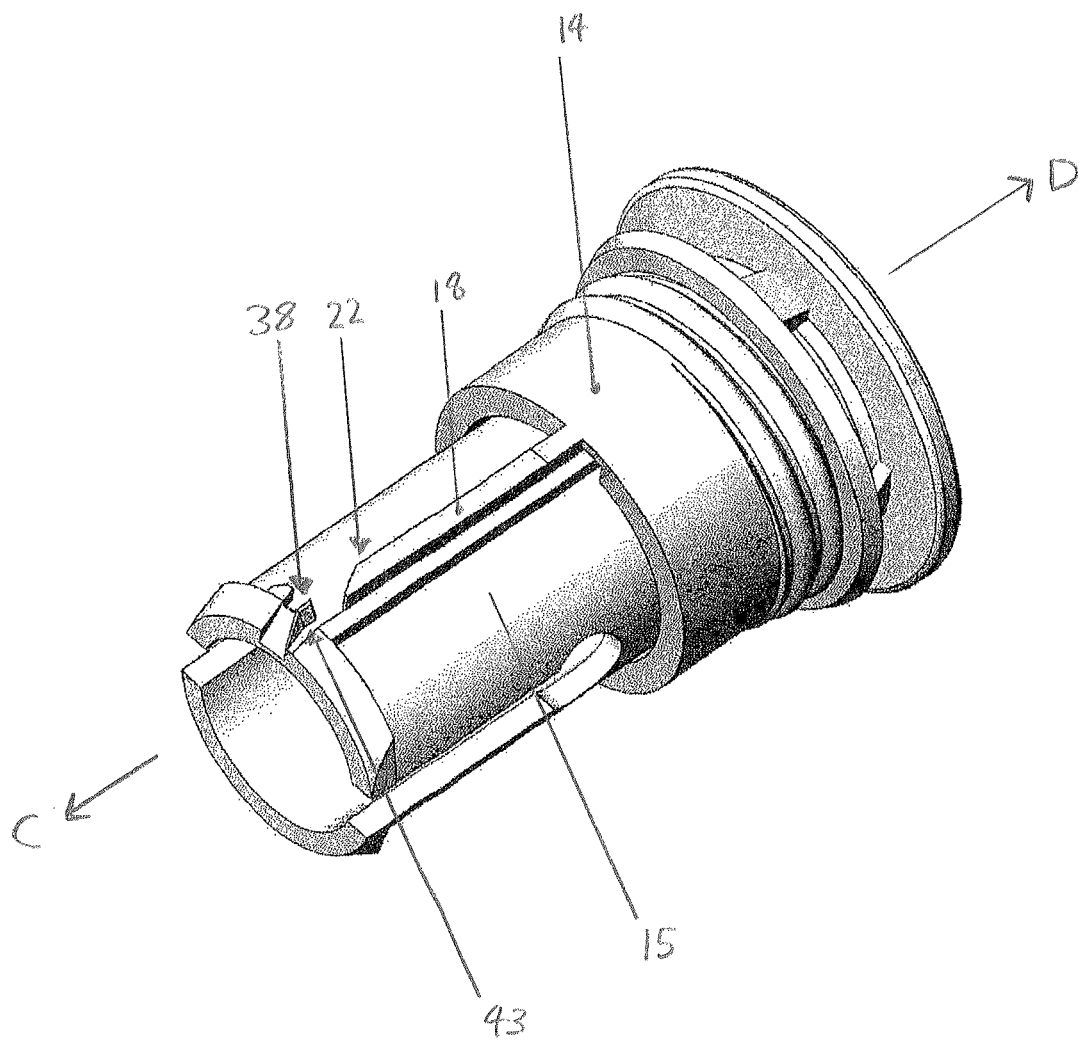
FIG. 5 illustrates, in perspective view, a mount and bushing of the apparatus of FIGS. 2 and 3 in a second configuration.

To remove the sheath, the user pulls on the sheath. This action releases the latch by moving the mount towards the injection end of the housing. This results in the beam 18 losing contact with the protrusion 21 on the mount, thus allowing the beam to resile to its second position 22, as shown in FIG. 5. The mount is now free to slide, urged by the spring 16, away from the injection end of the housing (in the direction of arrow D in FIG. 5). This results in the needle 6 being retracted within the injection end of the housing.

The apparatus will now be described in greater detail. FIG. 3 illustrates the housing 9 of apparatus 8. The sheath 7 and a plunger 12 of an enclosed syringe are also shown, as are the injection end 10 and plunger end 13 of the housing 9.

As shown in FIG. 4, the mount 15 is retained within the bushing 14 and is slidable within the bushing. The mount 15 and bushing 14 in FIG. 4 are shown in the same orientation as the apparatus in FIG. 3. Therefore, movement of the mount 15 towards the injection end 10 of the housing 9 is in the direction of arrow A. The internal diameter of the mount is adapted to fit around the syringe barrel 2. As the wings 5 of the syringe also abut the rear end of the mount 15, the syringe 1 and mount 15 move together.

The mount comprises a cylindrical mount body 23 with a front end 24 and a rear end 17. The front end 24 is provided with a passage 25 and a lip 26 extending radially outwards. The rear end 17 of the mount is provided with an annular mount ring or spigot 27. The lip 26 and the annular ring 27 serve as end points for the sliding motion of the mount 15 within the bushing 14.

The bushing 14 comprises a substantially cylindrical body 28 having a front end 29 and a rear end 30. The rear end 30 is provided with an annular bushing ring or spigot 31. The cylindrical body 28 is also provided with a screw thread 32 for screw-wise engagement with the housing (as shown in FIG. 2) and the annular bushing ring 31 which, as mentioned above, provides a stop to resist further movement of the bushing towards the injection end 10 of the housing 9. The stop may also prevent over-tightening when the bushing 14 is screwed into the housing 9.

Extending from the front end 29 of the bushing body 28, and along the outer surface of the cylindrical mount body 23, is the beam 18. One end 33 of the beam 18 is attached to the bushing body 28 whilst the free end 34 extends from the bushing body towards the injection end of the housing. The free end 34 of the beam 18 is provided with a first ramp 35 that cooperates with the lip 26 of the mount 15 to radially deflect the beam 18, as described below. The beam is further provided with a second ramp 36. The second ramp 36 cooperates with the protrusion 21 to deflect the beam 18 to a deflected third position 37 as described below.

The first ramp 35 and the second ramp 36 are contiguous but are angled with respect to each other as they deflect the beam 18 in separate directions.

The beam 18 is resilient in that it may be deformed so as to deflect radially outwards (as also discussed further below) and laterally as shown in FIG. 4. Here, the beam is deflected to one side, but still lies in substantially the same plane as the bushing body, such that it rests on an upper face 38 of the protrusion 21 on the mount 15. This is the initial position of the beam 18 before the sheath 7 removal procedure is commenced. The beam can be set into this deflected first position when the mount 15 is inserted into the bushing 14.

A spring 16 (shown in FIG. 2) is positioned between the rear end 17 of the mount 15 and the annular ring 31 of the bushing 14, to bias the mount 15 in the direction of arrow B, i.e. away from the injection end 10 of the housing 9, thus retracting the needle (within the injection end of the housing).

The front end 24 and the rear end 17 of the mount 15 extend beyond the front end 29 of bushing body 28 and the rear end 31 of bushing body 28. The overlapping nature of ends 24 and 17 allows the mount 15 to slide axially (in the direction of arrow A or B) within the bushing body 28 between said ends. This movement is under the influence of the spring 16 and may be further restricted by the action of the beam 18, as discussed below. The front end 24 of the mount 15 is provided with a lip 26. This serves to restrict the movement of the mount in the direction of arrow B as the lip contacts the front end 29 of the bushing to set the limit of this rearward motion of the mount.

To aid insertion of the mount 15 into the bushing 14, the mount body 23 is provided with opposing and compressible gaps 39 and 40. To aid alignment and prevent rotation of the mount 15 with respect to the bushing 14, a guiding ridge 41 is provided along the outer surface of the of the mount body 23, parallel to the longitudinal axis of the mount 15 and the bushing 14 (as represented by arrows A or B). This guiding ridge 41 cooperates with a corresponding notch 42 in the underside of the bushing body 28.

Rearward movement of the mount 15 (in the direction of arrow B) is thereby prevented when the beam 18 is in its deflected first position 19 as movement of the mount in this direction abuts the beam 18 against the protrusion 21.

The protrusion 21 is adjacent the lip 26 and is positioned such that the beam 18 is deflected away from the longitudinal axis of the mount 15 and bushing 14 when the beam 18 rests on the upper face 38 of the protrusion 21. When the beam is not deflected, i.e. it has resiled to its straightened second position 22, the beam is substantially parallel to said longitudinal axis over its entire length.

The width of the beam 18 and the position of the protrusion 21 are such that the beam can pass, albeit with a minor deflection, through passage 25 beneath a lower face 43 of the protrusion 21 when the beam 18 is in its straightened second position 22. The minor deflection is caused by the action of the second ramp 36 on the beam 18, as discussed below.

The underside of the beam 18 facing the mount body 23 is provided with a groove 44. This cooperates with a locating ridge 45 on the protrusion 21 of the mount 15, see FIG. 6.

FIG. 5 shows the mount 15 and bushing 14 in the first stage of sheath 7 removal. When the user wishes to inject a patient, it is first necessary to remove the sheath 7. This may be achieved, for instance, by the user gripping both the sheath 7 and housing 9 and urging the sheath 7 from the needle 6. As the sheath 7 is secured to the needle 6 by a friction fit, there is some resistance to its removal. Therefore, this action drags the mount 15 towards the injection end 10 of the housing 9 (in the direction of arrow C), thus compressing the spring 16. As the bushing 14 is fixed to the housing 9, the mount slides forward (in the direction of arrow C) with respect to the bushing 14. Thus, the beam 18 loses contact with the protrusion 21 and, as it moves rearwards (in the direction of arrow D), the beam resiles, snapping back to its straightened second position 22. Thus, the beam 18 is now substantially parallel to the longitudinal axis of the mount 15 and bushing 14 (and thus parallel to the movement of the mount 15 and bushing 14 represented by arrows C and D).

It will be appreciated that the force required to remove the sheath 7 from the needle 6 should be greater than the force required to compress the spring 16, otherwise the mount may not slide forwards as required.

The beam 18 is now free to pass beneath the lower face 43 of protrusion 21. This occurs when the sheath has been successfully removed and the mount moves rearwards, away from the injection end 10 of the housing 9 (in the direction of arrow D), under the influence of spring 16. This results in the needle now being substantially (or at least partially) retracted within the aperture 11 of the injection end 10 of the housing 9.

Figure 6:
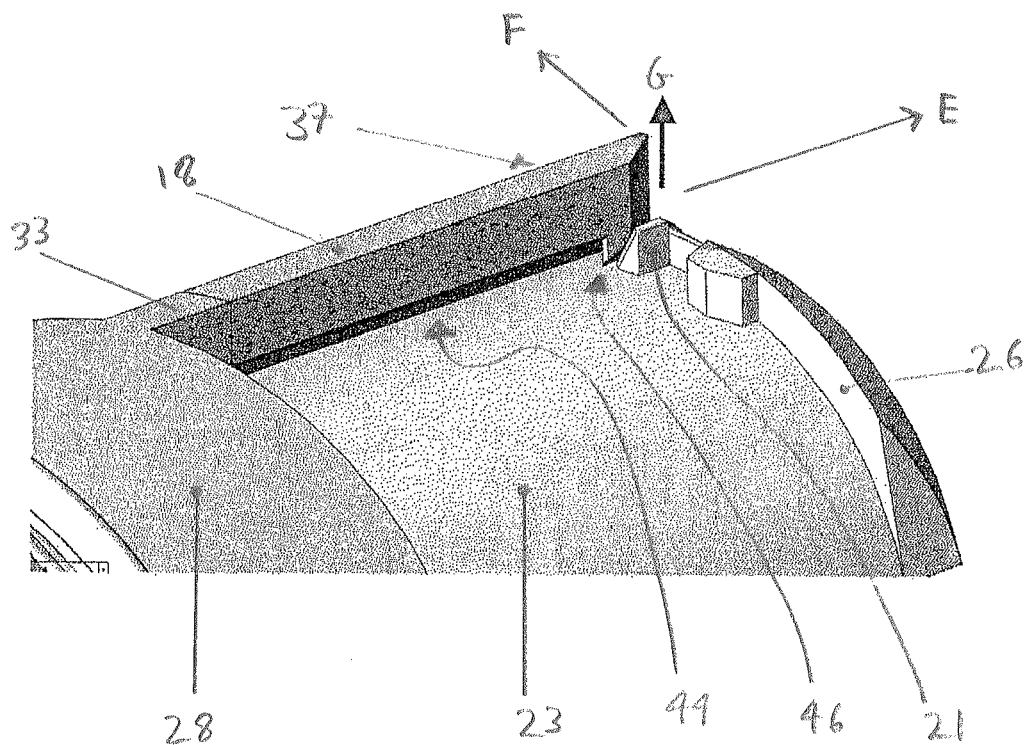
FIGS. 6 to 8 illustrate, in perspective view, a detail of the mount and bushing in various states of operation.
Figure 7:
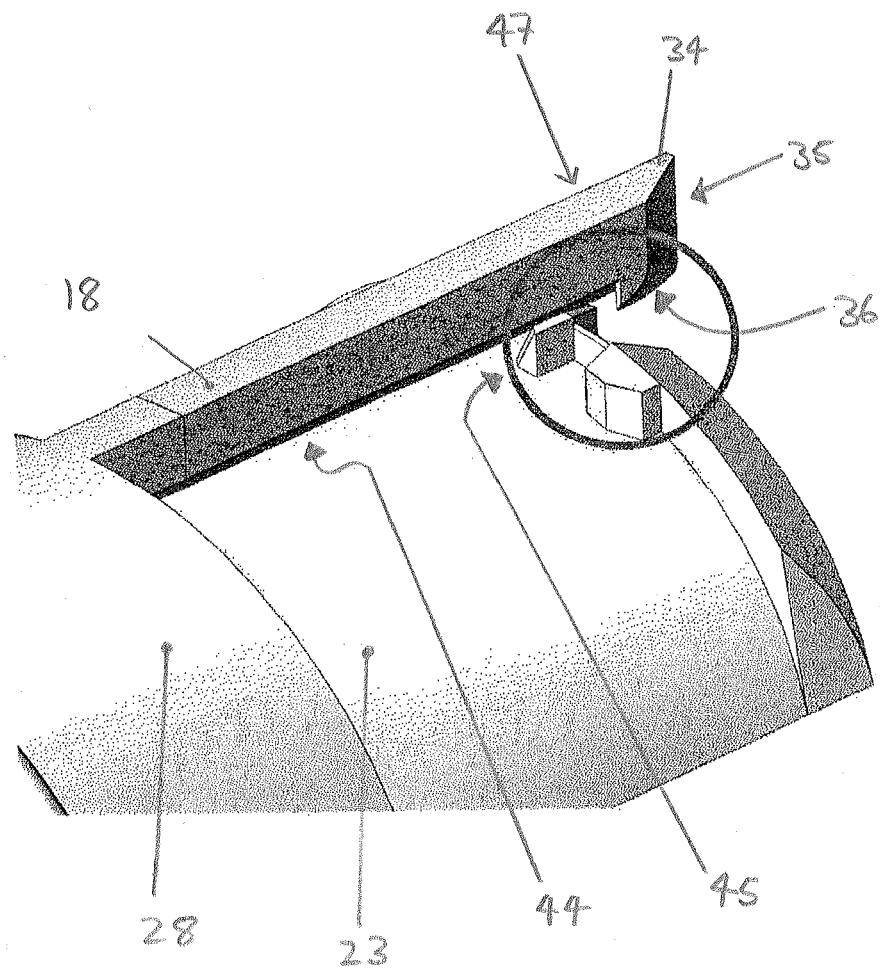
Figure 8:
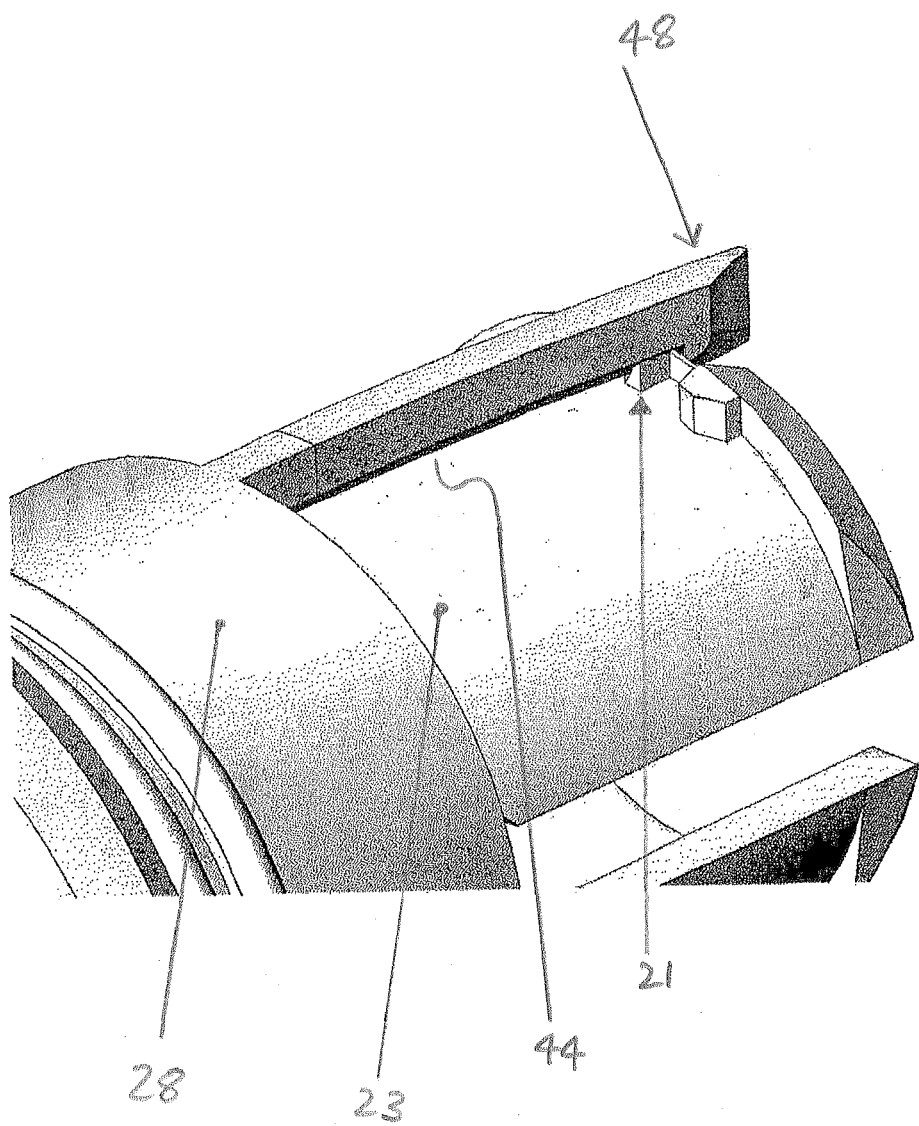

FIGS. 6 to 8 show the activation stage, once the sheath 7 has been removed and the needle 6 is exposed. FIG. 6 shows that as the mount 15 is urged rearwards by the spring 16, the beam 18 slides forwards, relative to the mount 15, towards the injection end 10 of the housing 9 (arrow E). When the beam 18 encounters the lip 26 of the mount 15, the first ramp 35 on the beam cooperates with the lip and the beam deflects radially outwards allowing the beam to ride up and over the lip to the fourth position 47 shown in FIG. 7.

At or around the same time as the beam 18 is deflected radially outwards to ride up and over the lip 26, the second ramp 36 cooperates with the protrusion 21 to deflect the beam 18 laterally into a deflected third position 37. This is represented by arrow F in FIG. 6. This deflection is relatively small compared to the deflection of the beam 18 onto the upper face 38 of the protrusion 21 seen in FIG. 4 and is in the opposite direction. The purpose of this deflection is that it serves to position beam 18 with respect to the locating ridge 45 on the protrusion 21. When the second ramp 36 on the free end 33 of the beam 18 has passed beyond the protrusion 21, the beam 18 resiles against the radial and lateral deflection and thus seats the locating ridge 45 into the groove 44 on the underside of beam 18, as shown in FIG. 8. Thus, further sliding of the mount 15 within the bushing 14 now occurs with the locating ridge 45 on the protrusion 21 running in the groove 44.

A hook 46 is formed at the free end 34 of the beam 18. The hook 46 catches on the lip 26 of the mount 15 when the mount slides towards injection end 10 of the housing 9. Thus, the hook prevents the mount sliding towards injection end of the housing beyond this fifth position 48, as shown in FIG. 8.

Without any action by the user, the bias of spring 16 urges the mount 15 rearwards away from the injection end 10 of the housing 9. Thus, the beam 18 extends further beyond the lip 26 of the mount 15, as show in FIG. 2. In this arrangement, the needle 6 is not exposed beyond the injection end 10 of the housing 9. This reduces the risk of an unwanted "stick" injury or contamination of the sterile needle 6.

When a user comes to inject a patient, the injection end of the housing is placed against the skin of the patient at a suitable injection site. The needle is still retracted within the housing. The plunger 12 is then depressed. The action of the plunger against the liquid contents of the syringe in turn urges the syringe barrel 2 towards the injection end 10 of the housing 9. At the same time, of course, the needle 6 is urged towards, and then beyond, the injection end of the housing. As the plunger is depressed, the needle passes beyond the injection end of the housing and pierces the patient's skin.

The movement of the syringe body also moves the mount in the same direction (i.e. towards the injection end of the housing) due to the action of the wings 5 against the annular ring 27 of the mount. However, the range of movement of the mount in this direction is limited, as the mount can only slide within the bushing in this direction until the hook 46 engages with the lip of the mount. Thus, the interaction of the hook 46 of the beam with the lip of the mount prevents the mount moving any further towards the injection end of the housing. Therefore, when the plunger is depressed, the mount is restrained by the hook from further movement towards the injection end of the housing.

The injection depth may be determined by the intended site of delivery. The length of the beam, together with the arrangement of the hook and the lip of the mount, may be set to achieve a desired injection depth.

It will be appreciated that the point of contact of the beam 18 in its deflected first position 19, with the protrusion 21 does not comprise a ramp, so as to ensure that the beam does not inadvertently ride up and over the protrusion.

The action of the hook 46 on the lip 26 may be augmented by the end of the locating ridge 45, nearest the free end 34 of the beam 18, catching on the protrusion 21 of the mount 15.

The apparatus may be made of a rigid plastics material. The apparatus may also be provided with means for locking the mount in an injection position, suitable for injection of a patient. In this injection position, the mount may be positioned towards the injection end 10 of the housing 9, thus exposing the needle beyond the aperture of the injection end 10 of the housing 9. This injection position may be at the engagement position of the hook with the mount.

The apparatus may be used, together with a pre-filled syringe (having a needle and a sheath) and means for assisting with the injection of medicament from the syringe, in an injection device.

FIGS. 9 to 14 illustrate an alternative sheath removal apparatus. The apparatus is for removing a sheath from a pre-filled syringe having a barrel and a needle, the sheath providing a sterile cover for the needle as shown in FIG. 1. The apparatus comprises a housing for enclosing the syringe barrel defining an injection end with an aperture sized to allow the sheath of an enclosed syringe to protrude therethrough. The apparatus also comprises means for retaining the syringe in the housing. Sheath removal means are also provided. These comprise one or more buttons positioned so that one or more cooperating wedges can be activated within the housing to press into a gap between the shoulder of the syringe barrel and the end of the sheath which adjoins said shoulder. The wedges are shaped so as to fit against the syringe shoulder and are provided with suitable edges or ramps adapted to urge the sheath from the needle as the wedges are driven radially inwards.

Figure 9:
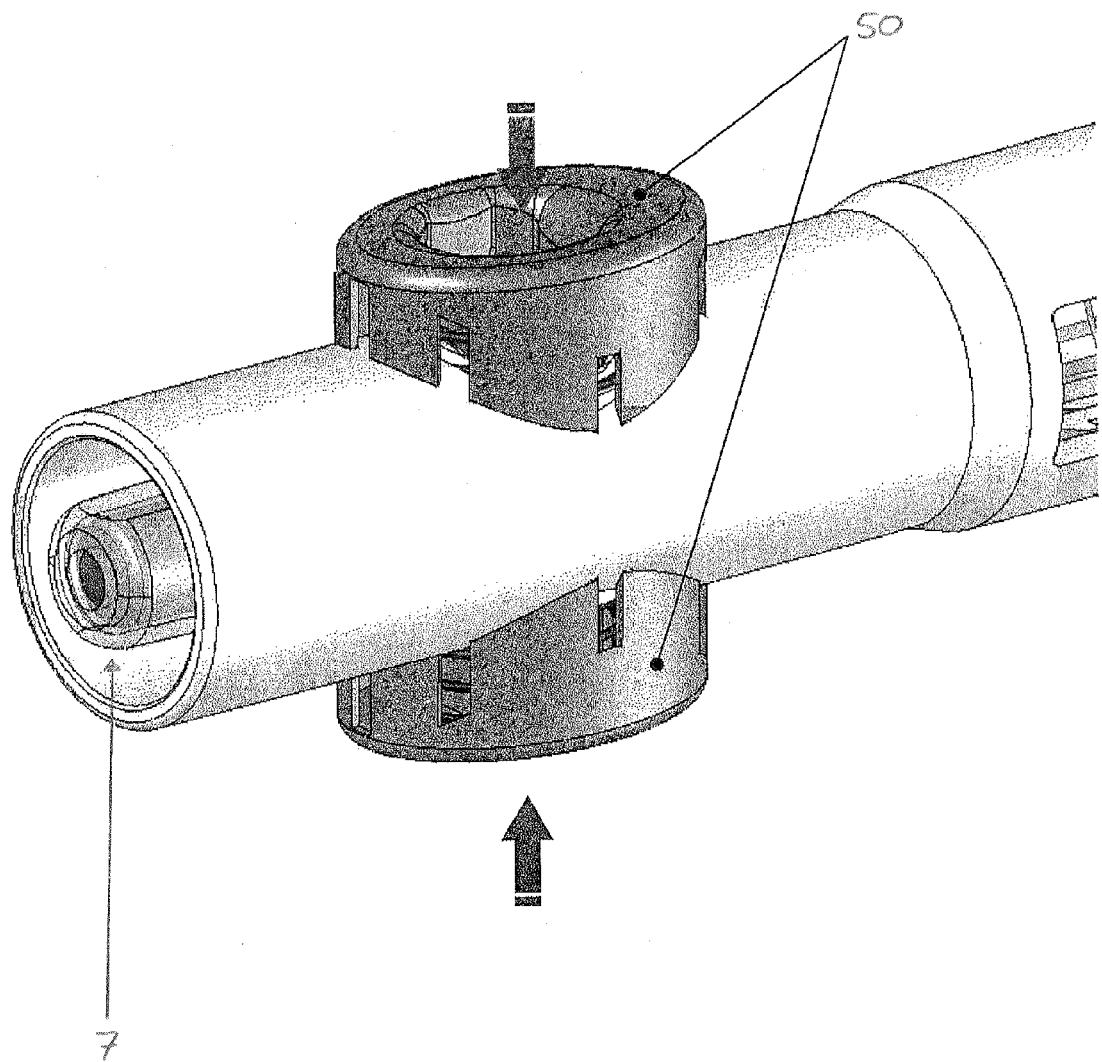
FIG. 9 illustrates, in a perspective view, an alternative sheath removal apparatus having buttons which drive wedges between a sheath and a syringe body.
Figure 10:
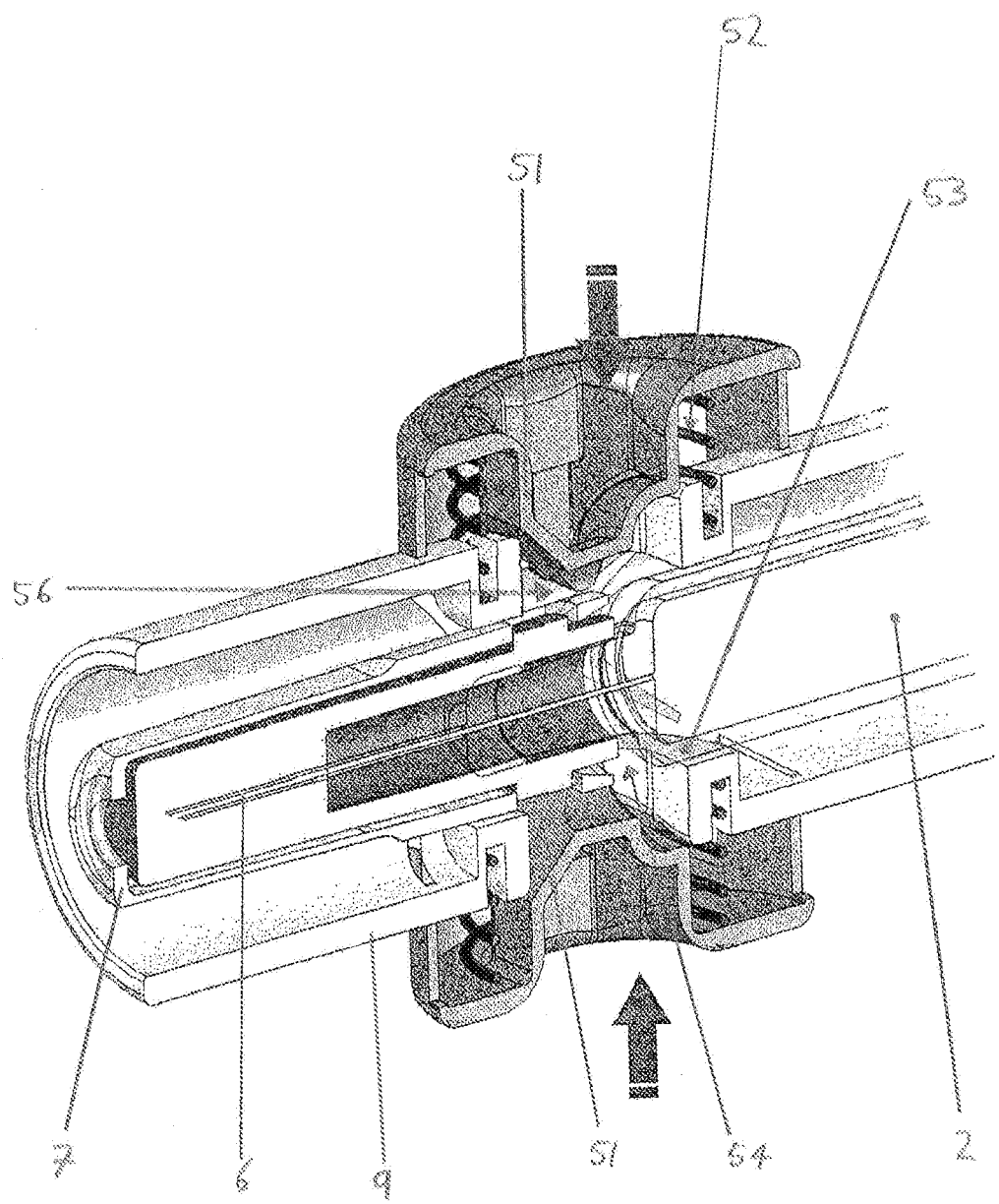
FIG. 10 is a cut-away section of the apparatus of FIG. 9.

FIG. 9 shows an overview of an embodiment of the housing 9 enclosing the sheath 7. Two activation buttons 50 are shown. In FIG. 10 it can be seen that pressing on the buttons drives wedges 51 radially inwards towards the needle and in the direction of the arrows shown and against the bias of a button spring 52. The shoulder 53 of the barrel 2 can also bee seen, as can the gap 54 and the needle 6. The edges 55 are curved and come to a sharp point.

Figure 11:
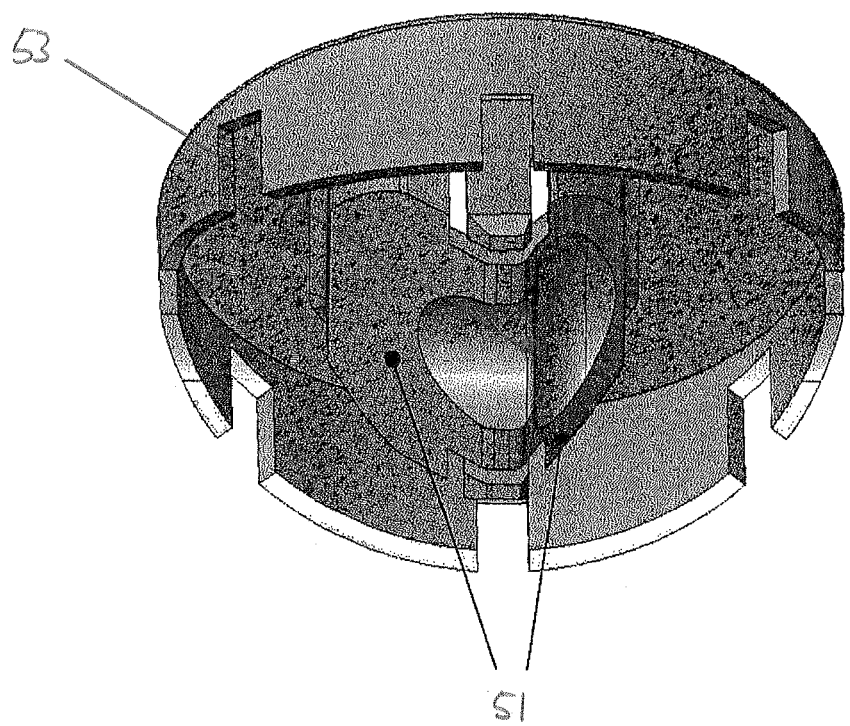
FIG. 11 shows the buttons of FIGS. 9 and 10 in more detail.
Figure 12:
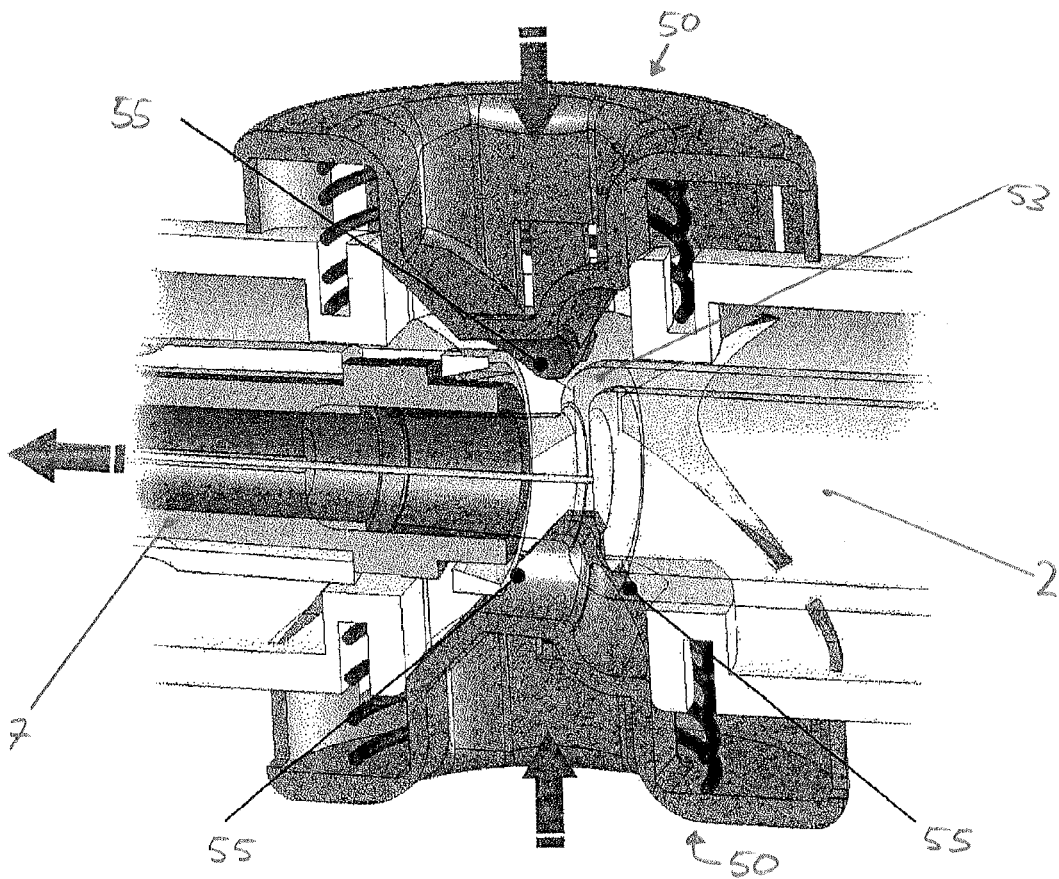
FIG. 12 shows a first stage of sheath removal, using the apparatus of FIG. 9.
Figure 13:
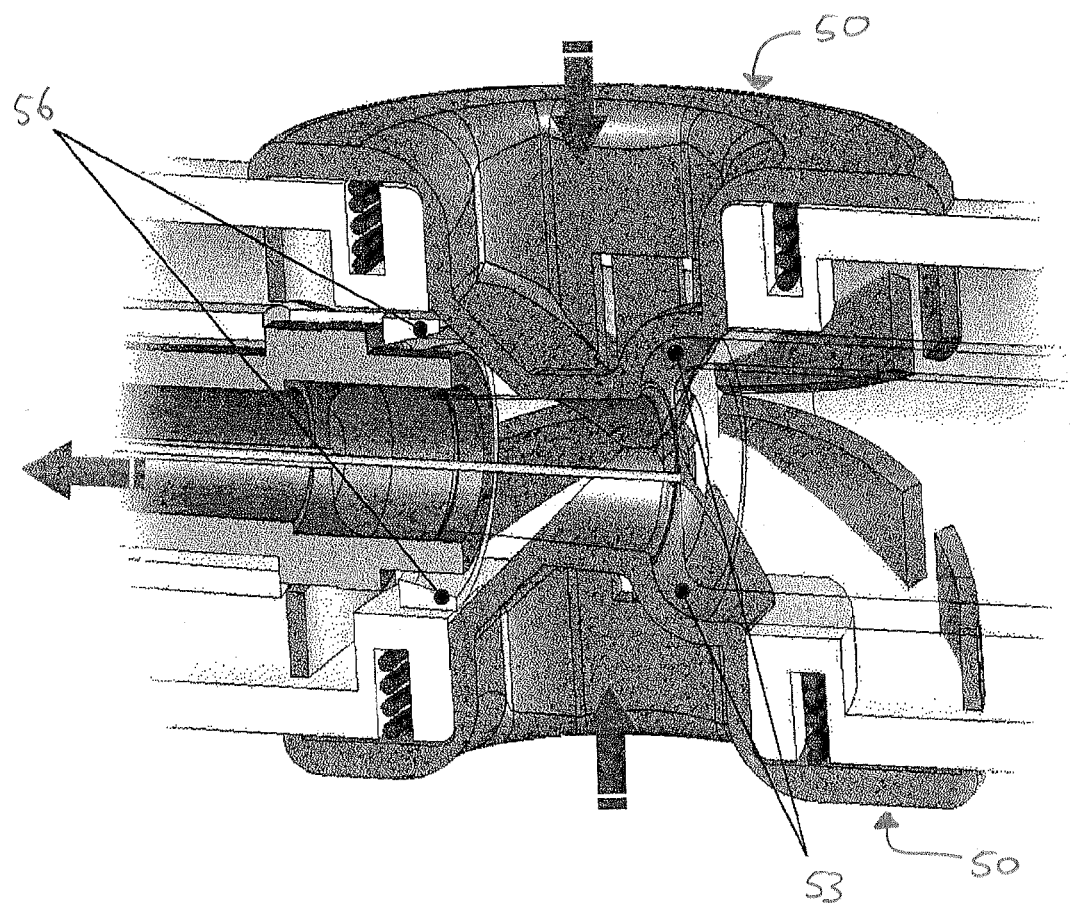
FIG. 13 shows a second stage of sheath removal, using the apparatus of FIG. 9.
Figure 14:
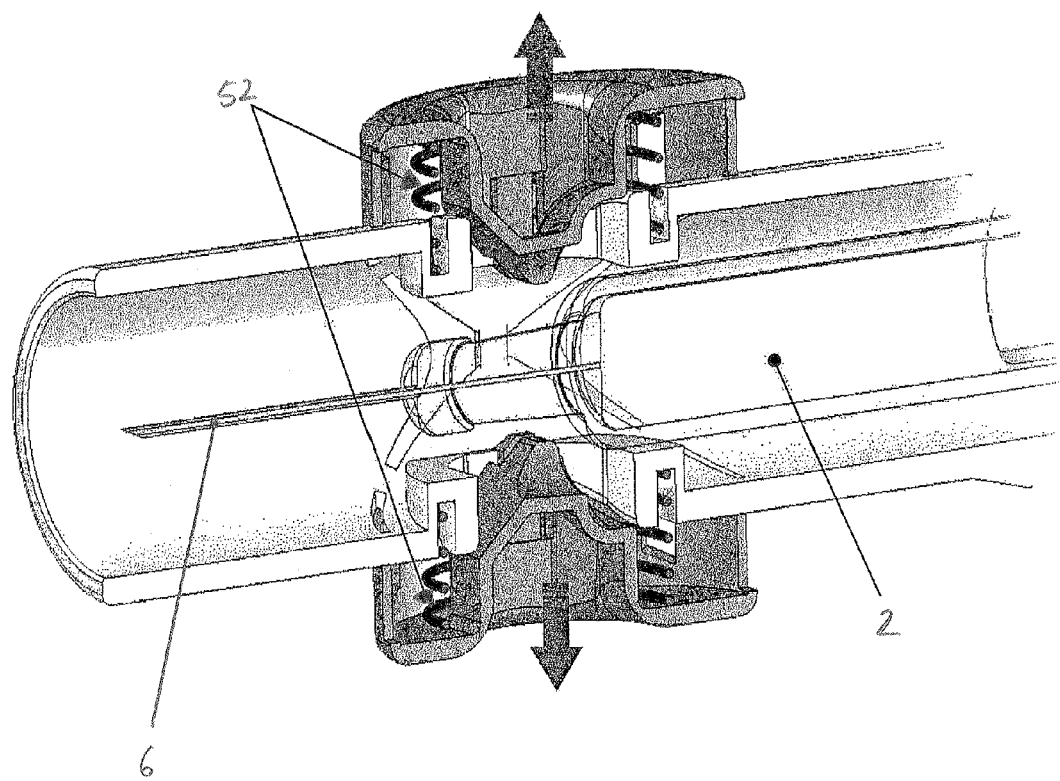
FIG. 14 shows the sheath completely removed, using the apparatus of FIG. 9.

FIG. 11 shows the buttons 50 in more detail with edges 55 for driving into the gap. FIG. 12 shows the buttons partially depressed. The edges 55 locate between the sheath 7 and the shoulder 53 of the sheath 7 as the buttons 50 are pressed by the user. Once the buttons 50 are fully depressed, see FIG. 13, the points 56 of opposing wedges 51 come together and the sheath 7 is urged off the needle, as shown in FIG. 14. A collar 56 is be provided to assist removal of the sheath.

It will be appreciated by the person of skill in the art that various modifications may be made to the above described embodiments without departing from the scope of the invention.

The invention claimed is:

1. Apparatus for facilitating removal of a sheath from a pre-filled syringe having a barrel and a needle, the sheath providing a sterile cover for the needle, the apparatus comprising:
    a housing for at least partially enclosing the syringe barrel and defining an injection end with an aperture configured to allow the sheath of an enclosed syringe to protrude therethrough;
    a syringe barrel mount for retaining the syringe in the housing and being slidable axially within the housing between positions towards and away from the injection end of the housing such that the syringe and the syringe barrel mount move together;
    a biasing mechanism for biasing the mount away from the injection end of the housing; and
    a latching mechanism that latches said mount in a latched position to prevent sliding of the mount away from the injection end of the housing, the latching mechanism being releasable from the latched position by sliding of the mount towards the injection end;
    the latching mechanism being arranged such that when the latching mechanism is in the latched position the sheath of the syringe is exposed through the aperture, and the biasing mechanism being arranged such that removal of the sheath will cause the mount to slide towards the injection end, and such that when the latching mechanism is released the biasing mechanism urges the mount to a position where the needle of the syringe is retracted within the injection end of the housing.

2. The apparatus of claim 1, wherein the latching mechanism comprises a bushing within the housing and within which the mount is retained, the mount being moveable axially within the bushing.

3. The apparatus of claim 2, wherein the latching mechanism further comprises a resilient beam connected to said bushing.

4. The apparatus of claim 3, wherein the latching mechanism further comprises a protrusion on the mount.

5. The apparatus of claim 4, wherein the beam extends axially towards the injection end of the housing and is deflectable, by engagement with the protrusion on the mount, into a first position to thereby latch the latching mechanism in the latched position.

6. The apparatus of claim 5, wherein the beam is resilable to a second position upon release of the latching mechanism.

7. The apparatus of claim 3, wherein the beam comprises a hook at the end proximal to the injection end of the housing, the hook extending radially inwards to engage the mount and thereby limit movement of the mount in a direction towards the injection end.

8. The apparatus of claim 1, wherein the biasing mechanism is a spring.

9. The apparatus according to claim 1 further comprising:
    an injection device attached thereto,
    said injection device comprising a pre-filled syringe having a needle, a sheath providing a sterile cover for the needle, and an assisting mechanism with the injection of medicament from the syringe.

* * * * *